(12) United States Patent
Pearlman

(10) Patent No.: US 7,688,428 B2
(45) Date of Patent: Mar. 30, 2010

(54) NON-CONTACT OIL SPILL DETECTION APPARATUS AND METHOD

(75) Inventor: Michael D. Pearlman, El Cajon, CA (US)

(73) Assignee: InterOcean Systems, Inc., San Diego, CA (US)

( * ) Notice: Subject to any disclaimer, the term of this patent is extended or adjusted under 35 U.S.C. 154(b) by 401 days.

(21) Appl. No.: 11/684,168

(22) Filed: Mar. 9, 2007

(65) Prior Publication Data

US 2007/0210262 A1    Sep. 13, 2007

Related U.S. Application Data

(60) Provisional application No. 60/780,976, filed on Mar. 10, 2006.

(51) Int. Cl.
*G01N 33/28* (2006.01)
(52) U.S. Cl. .................... 356/70; 357/445; 357/417; 357/419
(58) Field of Classification Search ............... 356/417, 356/317, 445, 70; 250/461.1
See application file for complete search history.

(56) References Cited

U.S. PATENT DOCUMENTS 6,744,503 B2 * 6/2004 Vo-Dinh et al. ............ 356/318

| | | | |
|---|---|---|---|
| 7,267,457 B2 * | 9/2007 | Ostler et al. | 362/294 |
| 7,400,405 B2 * | 7/2008 | Sadeghi et al. | 356/417 |
| 7,518,710 B2 * | 4/2009 | Gao et al. | 356/73 |

OTHER PUBLICATIONS

Photograph of Apr. 2004 prototypes.

* cited by examiner

*Primary Examiner*—L. G Lauchman
(74) *Attorney, Agent, or Firm*—Fitch, Even, Tabin & Flannery

(57) ABSTRACT

Apparatus for detecting the presence of a targeted group of hydrocarbons, such as diesel/fuel oil, lube oil, motor oil, hydraulic oil, jet fuel, mineral oil and crude oil in a highly reliable manner even though present at only extremely low concentration. A high power, pulsed light source is focused into a collimated beam that is reduced by a set of filters to a band of pulsed light within a precise set of wavelengths and directed vertically onto a target surface, such as a body of water. All but a precise band of light wavelengths returning to the apparatus are blocked so that substantially all light which then reaches an internal photodetector is within such precise band of wavelengths; as a result receipt of such light pro-grammed intervals following such pulses is indicative of the presence of a member of the targeted hydrocarbon group.

11 Claims, 2 Drawing Sheets

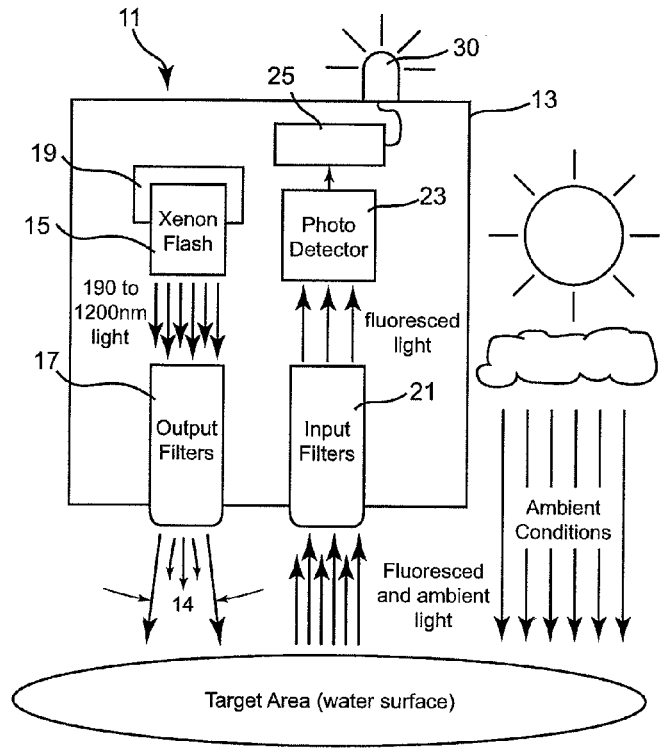
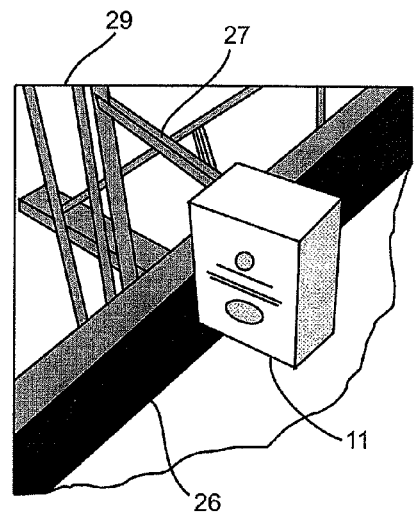
Fig. 1
Fig. 2
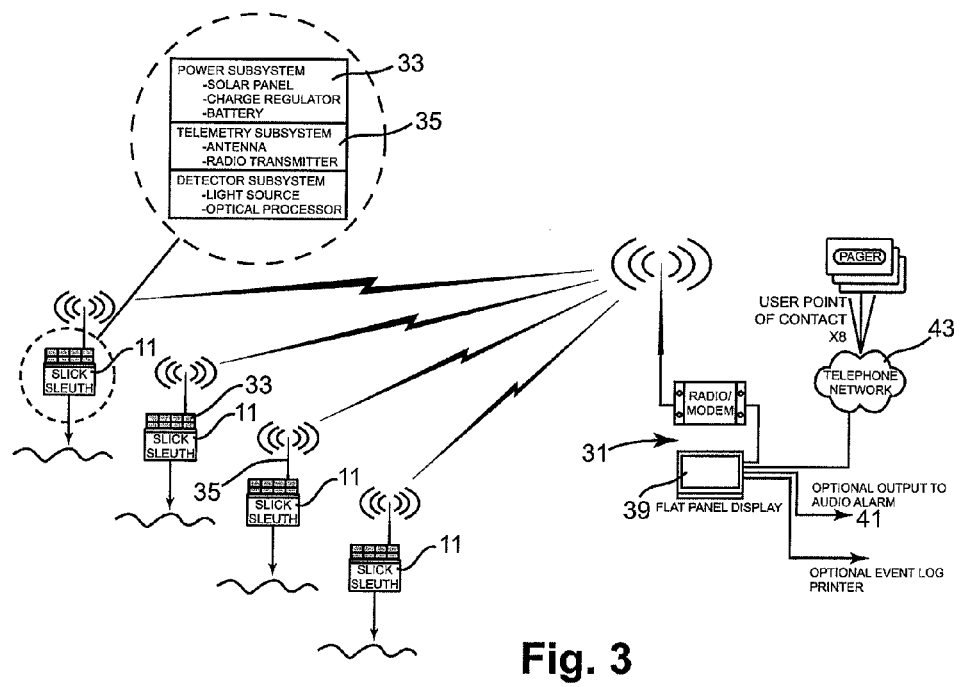
Fig. 3

NON-CONTACT OIL SPILL DETECTION APPARATUS AND METHOD

This application claims priority from U.S. Provisional Application Ser. No. 60/780,976, filed Mar. 10, 2006.

The invention relates to an apparatus and a method for detecting spilled or leaking pollutants, more particularly to such apparatus and methods that use monitors mounted above a target surface and effect non-contact monitoring to detect the presence of hydrocarbons or other organic contaminants that may be present, and still more particularly to systems and methods designed to monitor the surface of a body of water to detect hydrocarbons that may be floating on the water surface.

BACKGROUND OF THE INVENTION

Oil spills and leakages, both large and small, have become a major problem throughout the world. With continued dependence on fossil fuels and oil derivative products, there is more production, transportation, storage, and use of oils than ever before. Because oil spill and leakage prevention and response are growing concerns as a result of growth, demand, and the omnipresence of oil, new methodologies and technologies necessary to protect ourselves and the environment are being sought.

It is felt that the ability to detect petroleum spills, leakages and sheens in real time should allow response personnel to often contain pollution before extensive damage is done to the wildlife, environment, etc. Successful prevention and/or minimization of a spill or leakage as a result of real time detection will provide a substantial benefit not only to the entity responsible for the spill or leakage, but also to all waterway stakeholders, the surrounding environment, and society as a whole. Previous in-water systems which were developed for monitoring bodies of water have required substantial maintenance as they were susceptible to bio-fouling and to debris inherent within water deployment. Likewise, flow-through systems were found to be susceptible to bio-fouling and oil staining on the sampling tube. Accordingly, better automated systems that will remotely monitor for such petroleum spills, leakages and sheens and provide prompt notification and/or alarm upon detection of a spill, leakage or the like have continued to be sought after.

SUMMARY OF THE INVENTION

The invention provides a reliable, economical, optical, non-contact oil-on-water petroleum detection station which incorporates improved technology that will provide a reliable detection signal even when only trace amounts of petroleum or its products are present on a target surface or in water near the surface, e.g. of only a slight sheen on the water surface. The system employs a downward-focused optical sensor that is installed above the target surface to provide clearance between it and the target, e.g. sufficiently above a tidewater surface so as to operate effectively during high tide and low tide. For example, the design may be such that the apparatus is capable of effective operation at a distance as great as 5 meters above the target surface. The invention is suitable for monitoring for spills around, in and on offshore structures, buoys, coastal installations, ports, harbors, piers, marine terminals, culverts including sumps and outfalls, inland waterways and the like and is also valuable for monitoring for leakages from land-based installations, such as tank forms. Moreover, the invention is capable of effective operation even in regions of fairly high velocity water movements. The invention can provide continuous or substantially continuous monitoring, and when used in a large lake or an ocean environment, it is immune to wave action.

More specifically, the invention utilizes a high-power lamp and filters and focuses pulsed light of a desired wavelength into a conical beam that is projected downward onto the target area so as to cause fluorescence of suspected contaminants should such be present. Fluorescent light emanating from any hydrocarbon present in or on the target surface is then detected by photodetector means or other appropriate detection means. It has been found that by limiting the pulsed light that reaches the target surface to one set of wavelengths and by also limiting the returning light that will reach the photodetector to a different set of wavelengths that will encompass fluorescent light of interest, a reliable sensor can be created that will very effectively recognize a target set of hydrocarbons, ranging from light lubricating oil to crude oil and mineral oil, which target set essentially encompasses the entirety of potential spills, leaks and discharges that are considered to be of most interest, while effectively minimizing background interference.

BRIEF DESCRIPTION OF THE DRAWINGS

FIG. 1 is a schematic view showing the essential operation of the invention.

FIG. 2 is a perspective view of one embodiment of the invention shown mounted above a cooling water spillway or the like.

FIG. 3 is a schematic view showing how a plurality of remote detection stations can be used and linked to a base station by radiotelemetry.

FIG. 4 is a perspective view showing use of a detection station to monitor an underground flowing stream through a metal grate or the like.

DETAILED DESCRIPTION OF THE PREFERRED EMBODIMENTS

Figure 4:
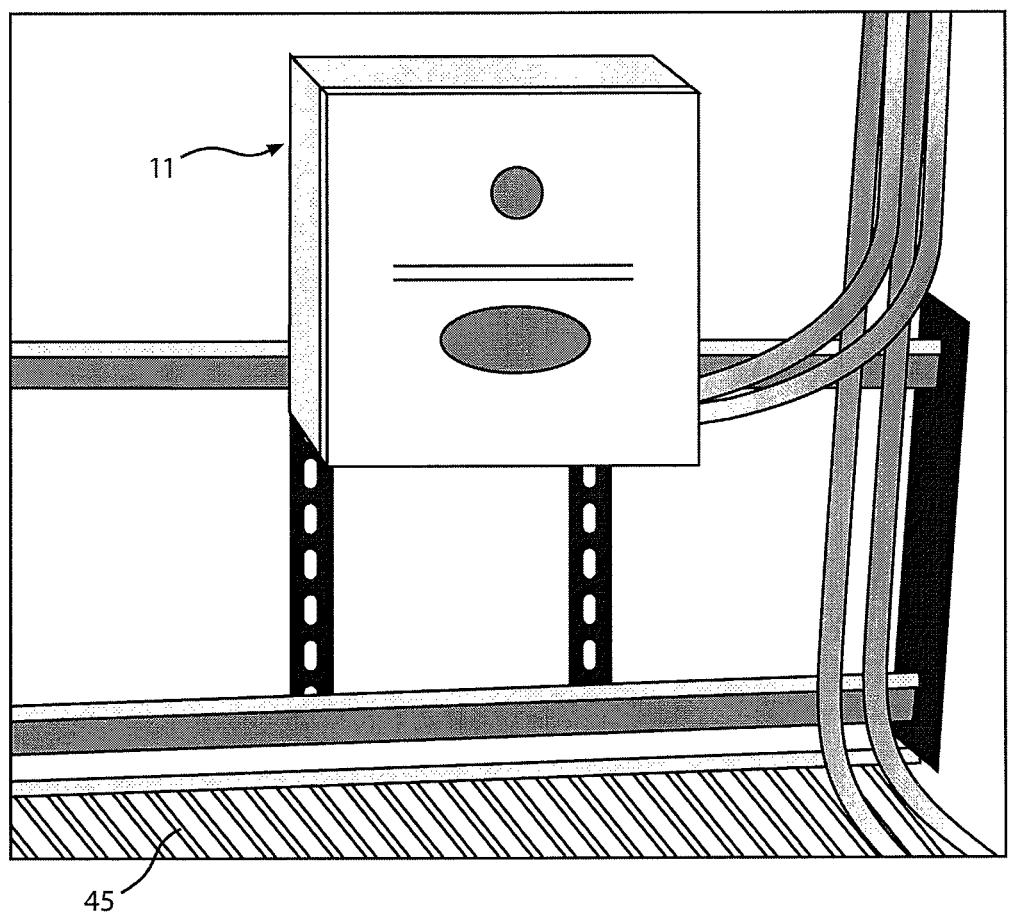

Oils and other organic compounds are known to fluoresce; thus, effective detection apparatus can be used to detect the presence of oil by appropriately exciting a floating oil film and measuring resultant fluorescence. Fluorescence is an optical phenomenon which occurs when a compound absorbs light at one wavelength and then emits light at a longer wavelength. When fluorescent compounds are bombarded with light, some of the light energy is absorbed through the excitation of electrons to higher energy states. Once the light source is removed, the excited electrons fall back to their ground state giving off light in the process. This process is very similar to what makes glow-in-the-dark materials possible, except it takes place in a much shorter period of time. Because some energy is lost as heat in the absorption-emission process, the wavelength of the emitted light is always longer than the wavelength of the absorbed light. Typically the absorbed light for hydrocarbons is in the ultraviolet range, and the emitted light will extend into the visible range.

Detection and quantification of hydrocarbons and other organic substances by fluorescence emission spectroscopy (FES) is possible and is founded upon proportionality between the amount of emitted light and the amount of a fluoresced substance present. When energy in the form of light, including ultraviolet and visible light, is directed onto a target surface, e.g. a body of water, fluorescent substances present, i.e. floating on and therewithin, will absorb that light energy, and once said source is removed, such substances will then emit such energy as light having a longer wavelength than the absorbed light. As a result, the presence of such fluorescent substances is then determinable from knowing the amount of directed light and the amount of emitted light that is detected and measured by a photodetector. The initial light, as a pulsed beam, is directed through an optical light filter that is designed so that only light of a desired set of wavelengths is transmitted and directed toward the surface of interest. Wavelength is generally given in nanometers ("nm"), and the wavelengths of the directed light pulses are referred to as the excitation wavelengths. The returning fluorescent light that is given off by substances on and in the target surface is similarly screened through a filter so that only emitted light measuring within a desired spectrum of wavelengths will reach the photodetector. This spectrum will include the wavelengths of fluorescence of hydrocarbons, which are referred to as the emission wavelengths, and they are generally also reported in nanometers. The detection process is generally referred to as FES.

The ability to measure specific categories of such substances at only low concentrations is particularly desired, and it has been surprisingly found that such is made possible by using a filter package that will provide a pulsed beam of light having a narrow range of excitation wavelengths in combination with another filter package that will block all light except that which falls within a group of specific emission wavelengths from reaching the detector. It has been found that, using such a combination of these two sets of wavelengths, allows very effective detection of even low-level amounts of a desired class of potential pollutants from light lubrication oils to crude oil. More specifically, it has now been found that this specific group of hydrocarbons which constitute the majority of potential contamination occasions can be excited by absorbing light pulses of a wavelength between about 225 and 300 nm, and that they will then emit light in the narrow range of about 320 to 400 nm. Consequently, it has been found that using a combination of filter packages limited to these two sets of wavelengths will provide the basis for a very effective monitoring system by minimizing, i.e. screening out, the background noise effect that has heretofore proved to be most problematic to overcome when the concentrations of such pollutants are at very low levels.

In contrast to earlier in-water systems, it has been found that a detection apparatus having the features of the present invention, i.e. a downward looking, non-contact optical sensor can now be very effectively installed above any target surface area where it will be totally free of these fouling effects that adversely affected such prior systems. Moreover, it has been found that fluorescence generating and measuring instruments operating as a part of such an apparatus that is located as high as 5 meters above a target surface can effectively detect the aromatic components of petroleum hydrocarbons that are present even at very low concentrations, i.e., parts-per-million. Basically, the optical measurement technique that is utilized directs a beam of high power, pulsed light in a collimated conical pattern onto the target surface so that it comes into contact with materials present thereon and monitors for returning light that would be created if certain pollutants were present, e.g. floating on a water surface. It is constructed to detect scattered fluorescent light whenever such is given off, which light is indicative of the presence on the surface of a specific group of prospective pollutants being monitored.

Schematically illustrated in FIG. 1 is an apparatus 11 for detecting floating pollutants of organic material which includes a plurality of operative components that are supported in or on a structure, e.g. an enclosure 13. Depending upon the environment in which the apparatus will be intended to operate, the enclosure 13 can take any of a wide variety of suitable forms. Because the usual intended use of the detection apparatus is outdoors, the supporting structure will usually be an enclosure 13, and preferably one which is weatherproof, rustproof and of rugged construction. Stainless steel and/or appropriately coated steel are examples of materials that might be employed. If it is intended that the apparatus will be employed in a hazardous or explosive environment, such an enclosure would be constructed so as to be vaporproof and/or to have a compatible air-purge system. The apparatus 11 may be designed to utilize external AC power, or it may be designed to operate with internal or external DC power. For example, it could utilize a separate DC power system that is housed in a separate weatherproof enclosure which is either collocated with the apparatus or perhaps installed at a nearby location where it would receive optimal exposure to sunlight for solar recharge of a battery contained therein.

Output data generated by the detection apparatus 11 can be transferred via hardwire to a desired location or control station; alternatively, wireless data communication, e.g. spread spectrum radio, satellite, or GSM/cellular may be included as a part of a separate DC power system. Disposed within the enclosure 13 of the apparatus 11 is a high power (preferably at least about 60 watts) light source 15, preferably a Xenon strobe or flash lamp, that will produce pulsed light in the wavelength range of about 190-1200 nm. The light output from such lamp is filtered through an output filter package 17 that is so selective as to allow only light between about 225 and about 300 nm to pass. Combined with this light source 15 and the filter package 17 is a parabolic reflector or other focusing means 19; the reflector and lamp are arranged to provide a conical beam of light that is directed toward the surface of the target surface located therebelow. Although illustrated only schematically in the simplified schematic shown in FIG. 1, the preferred parabolic reflector 19 for focusing the pulsed light beam effectively collimates the pulsed beam of light of defined wavelengths into a cone of light rays having the angle of incidence for impingement on the target surface that has been found to be most effective. Preferably a cone having an apex angle of about 13° to about 15° is used.

As earlier stated, the enclosure 13 can be mounted up to 5 meters above the target surface, and it is not important that the beam be directed exactly vertically downward so that the light hits at precisely 90° to the target surface. For example, the lens 19 may spread the light as a 13-15° cone focused downward onto the surface. Preferably, the alignment is such that the centerline of such cone is aligned to within about 7° of vertical. If the target is a body of water, it can be relatively quiescent, such as a pond or lake, or it can be a fairly rough part of an ocean or sea. It can also be a moving stream, either at ground level or underground, so long as there is optical contact between the enclosure and the surface of the water. For land-based installations, the target surface may be one of cement or concrete or even hard-packed earth. Hydrocarbons, including lube oil, motor oil, hydraulic oil, diesel fuel, jet fuel, kerosene, mineral oil, various process oils and heavy fuel oil, if present in the target area, will fluoresce when contacted by the downward directed light pulses, i.e. upon absorbing energy from a pulse, at the end of the pulse, the hydrocarbon molecule will subsequently emit light of a characteristic wavelength between about 320 and about 400 nm.

By regulating the angle of incidence at which the directed beam light contacts the target surface to within about 10° of vertical, and preferably within about 7°, fluorescent light will be emitted when a pollutant of this class is present on the target surface and will return to the region of the enclosure 13, as depicted in FIG. 1 in a sufficient amount, to afford its detection. An input filter package 21 is constructed so as to block the passage of all light other than that falling within an emission wavelength range of about 320 to about 400 nm. As a result, substantially all of the light that exits from the filter package 21 and enters a photodetector 23 will be light that was emitted as a result of fluorescence from hydrocarbons that are present. Accordingly, this arrangement very effectively filters out at least the major portion of noise and other incidental light rays while allowing the passage of substantially all emitted light returning in this direction that will be evidence of the presence of any substantial amount of a targeted pollutant.

The photodetector 23 that is employed is available as a state-of-the-art component. Such planar photodiodes are commercially available items that are capable of recognizing and quantitating light rays in the wavelength range of 300-400 nm. Preferably they should be able to function in a detector circuit that will operate on either AC or DC power. The output from the photodetector 23 is linked to an analyzer and signal processor 25 in the enclosure 13, which incorporates firmware to assure reliable detection while eliminating false detections. It is able to quickly determine whether the presence of a significant amount of hydrocarbon is being sensed and detected in response to each pulse of light being directed against the target surface.

Very generally, the analysis that will show the detection of hydrocarbons on or near the surface is predicated upon differential measurement, i.e. based on the anomalous signal return within an expected target time period that will occur when oil is present, as opposed to when there are no hydrocarbons present. When hydrocarbons are indeed present, a signal return will be detected that is proportional to the polyaromatic hydrocarbons (PAH) which are contained in all of the petroleum products here of interest, that may be present within the viewed or sampled test area.

The frequency of the pulsing of the high power Xenon strobe or flash lamp 15 can be adjusted depending upon the situation where the monitoring is occurring. For example, if continuous sampling/monitoring is desired, the strobe may be set to fire twice each second, and the detector 23 will be accordingly programmed to synchronously focus upon each pulse for detection. In another situation, it may be satisfactory to place the detection apparatus in a five second sampling rate mode where the strobe will create ten pulses at 100 millisecond (msec) intervals each five seconds, with the detector being likewise programmed to focus upon such.

It is contemplated that a major location of interest for such detection apparatus will be in ports and harbors, as well as in land-based installations, such as those using substantial amounts of cooling water, and those storing and/or transporting substantial quantities of such hydrocarbons. Depicted in FIG. 2 is an example of one such installation where a detection apparatus 11 is mounted on a pier or channel at a location about 3 meters above the water level via a support bracket 27 that is preferably slidably fixed to a vertical post 29 that is mounted along the edge of a pier or channel structure 26. In an installation such as this, there would commonly be a source of AC power, and the analyzer could be hardwired to some central control station. It may be desirable to optionally provide the enclosure 13 with an audible or visible alarm 30, e.g. a flashing light, that would signify the detection of pollutants of a certain minimal concentration at the apparatus itself, as well as sending this information to some central control station.

Illustrated in FIG. 3 is an arrangement where a plurality, e.g. four, remotely located detection stations 11 are individually linked to a base station 31. Each monitoring station 11 would monitor for hydrocarbons on the water surface at a preset schedule which might be set at any integral from ½ second to 60 minutes or more, depending upon the particular situation. Each of the stations 11 would be essentially self-contained; for example, a solar power supply 33 might be mounted on and/or in the enclosure 13 that would include a solar panel, a charge regulator, and a rechargeable battery. The enclosure 11 would include the light source 15 and optical processing package hereinbefore described, and there would also be a telemetry subsystem 35, including an antenna and a radio transmitter.

The base station 31 would typically include a wireless network controller which might be programmed to poll each of the remote monitoring stations 11 on a regular basis. The results, upon being received by wireless from the individual stations 11, would be collated and fed into a flat panel display 39 so as to be immediately available at the base station 31. Such data received would likely also be fed to a printer to keep a regular log of the input from all of the remote stations 11; a further analyzer in combination with the flat panel display would operate a visible and/or audible alarm 41 at the base station 31 upon the detection of a significant quantity of floating hydrocarbon that might be indicative of a spill or other such discharge. The appropriate alarm 30 might also be activated at the monitoring station itself if it was not already activated. Moreover, the system could be connected to a programmed pager/phone system 43 that would send out a prerecorded message to a responsible person or persons upon the occurrence of such an event. The use of such a series of remote monitoring locations can effectively provide highly reliable detection of floating PAH as a result of such a collimated pulsed UV light source being absorbed by PAH, which subsequently results in the emission of fluorescent light when a targeted pollutant is present. This highly reliable detection apparatus 11 has been shown to be effective in detecting only very small amounts of oil and thin sheens of oil, and it can even detect emulsified oil at concentrations of 0.1% and below.

As previously mentioned, the use of such a detection apparatus 11 is not limited to ports and harbors or the like, but it is effective wherever there can be line of sight access between the apparatus and a target surface. Illustrated in FIG. 4 is an arrangement where the detection apparatus 11 is deployed vertically above a cooling water catchbasin or outfall that is covered by metal grating 45. It has been found that the presence of such grating 45 does not interfere with the basic detection process, even though some percentage of the collimated beam of pulsed light will not reach the underlying water surface. It has been found that the sensitivity of the overall system is such that it will still adequately function in such an embodiment, and it will effectively detect the presence of floating hydrocarbons on a water surface some 3-5 meters below the undersurface of the detection apparatus 11 by focus through the grating.

Figure 5:
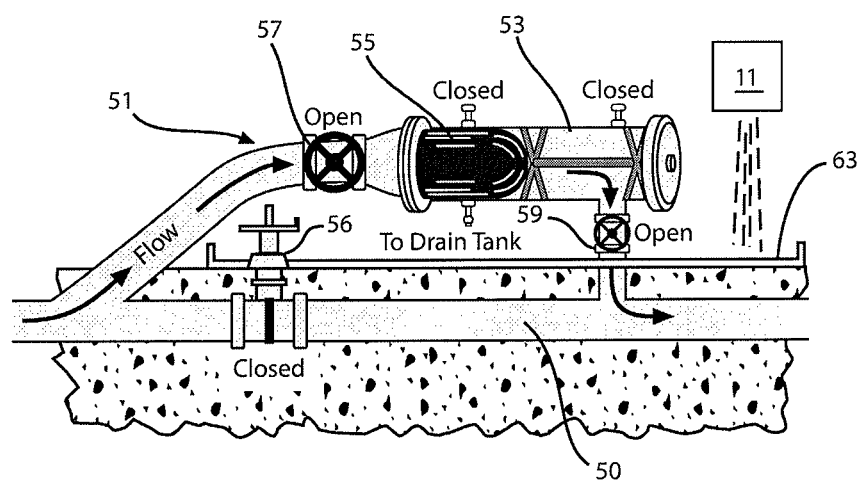
FIG. 5 is a schematic view of a pipeline station where a detection system is installed.

As previously indicated, for land-based operations, the target surface may not be a water surface, but may be one associated with the storage and transportation of hydrocarbons. In this respect, it may be a cement or concrete surface, or even one of hard-packed dirt. For example, where hydrocarbons are stored in bulk form in tanks, one or more such tanks will be surrounded by a dam, sometimes referred to as a "bundwall", and the volume within the enclosure will be more than the volume of the largest tank in case leakage should occur. However, by mounting a detection apparatus in the vicinity, early detection of any leakage can be made, which would present the opportunity to stem the flow of hydrocarbons from a leaking tank, and thus obviate the need to pump a large volume of leaked hydrocarbons for reclamation. Moreover, in the transportation of oil by long distances via pipelines, there are often a number of remote stations that are generally unattended for long periods of time. These may be stations such as satellite pumping stations where the pressure of the flowing stream is rebuilt after having traveled a certain number of miles, or there may be stations such as that illustrated schematically in FIG. 5 where a cleaning pig may be launched into or retrieved from a hydrocarbon pipeline. Depicted schematically in FIG. 5 is such a pipeline pig retrieval station 51 positioned at a desired location along a main pipeline 50 which includes a number of valves that could be subject to leakage, in association with a trap 53 for receiving the pig 55 when it arrives. For example, the main line valve 56 would be closed, and the valve 57 to the trap and a bypass valve 59 are opened when a signal is received that a pig 55 is nearing the retrieval station. Then, once the pig 55 has arrived, the isolation valve 57 and the bypass valves 59 are closed, and the main line valve 56 is again opened. Once the trap is drained, removal of the pig from the receiver proceeds. By monitoring these remote pipeline stations through the incorporation of a detection apparatus 11 located above a shallow catch basin 63, early warning can be obtained should hydrocarbon leakage occur at that particular station 51 so personnel can be quickly dispatched to remedy the problem at a very early stage.

Although the invention has been described with regard to certain preferred embodiments which constitute the best mode presently known to the inventors for carrying out their invention, it should be understood that various changes and modifications as would be obvious to those having ordinary skill in its art may be made without deviating from the scope of the invention which is set forth in the claims that are appended hereto.

Particular features of the invention are emphasized in the claims that follow.

The invention claimed is:

1. Apparatus for detecting floating pollutants from the class consisting of diesel/fuel oil, lube oil, motor oil, hydraulic oil, jet fuel, mineral oil and crude oil, which apparatus comprises:
a structure for mounting vertically above the surface of a body of water,
a pulsed light source supported by said mounting structure,
means supported by said mounting structure for directing said pulses of light from said source downward toward said water surface, and for filtering said pulses to produce a beam of light, limited to wavelengths between about 225 and 300 nm, which beam is an outwardly spreading cone of light rays having an apex angle of about 13° to about 15°,
sensor means supported by said structure for detecting fluorescent light that would be emitted from said pollutants on said water surface,
filter means supported by said structure that allows direct line of sight passage from said water surface to said sensor means of only light having a wavelength between about 320 to 400 nm,
means for analyzing data detected by said sensor means to determine the presence of even small quantities of floating pollutants within said class, and
means for promptly reporting and/or producing a signal or alarm when said analyzed data indicates the presence of any significant amount of one said pollutant.

2. The apparatus according to claim 1 wherein said directing means comprises a parabolic reflector.

3. The apparatus according to claim 2 wherein said structure is an enclosure in which said parabolic reflector and said pulsed light source are located.

4. The apparatus according to claim 1 wherein the enclosure is mounted such that the centerline of said cone is aligned at an angle of not more than about 7° from vertical.

5. The apparatus according to claim 1 wherein said pulsed light source is a high power Xenon strobe lamp.

6. A method for detecting pollutants from the class consisting of diesel/fuel oil, lube oil, motor oil, hydraulic oil, jet fuel, mineral oil and crude oil floating on a water surface, which method comprises:
mounting a structure about 3 to 5 meters vertically above a target water surface,
activating a light source carried by said structure to produce pulses of light,
directing said pulses of light downward toward the water surface through filtering means to produce a pulsed beam of light that is limited to a first set of wavelengths between about 225 and 300 nm, which beam is an outwardly spreading cone of light rays,
detecting fluorescent light emitted from said pollutants floating on the underlying target water surface using a sensor in combination with filter means that allows direct line of sight passage from said pollutants to the sensor of only light having a wavelength within a second set of wavelengths between about 320 to 400 nm, and
analyzing data generated by said sensor to determine the presence of even small quantities of floating pollutants within the targeted class that when so activated by such pulsed light will emit fluorescent light within said second set of wavelengths.

7. The method according to claim 6 wherein a signal or alarm is produced when said analyzing shows detection of any significant amount of such a pollutant in such targeted class.

8. The method according to claim 6 wherein said directing creates a cone of light rays which has an apex angle of about 13° to about 15°.

9. The method according to claim 8 wherein the centerline of said cone is aligned within about 7° of vertical.

10. The method according to claim 9 wherein said light pulses are spread outwardly in said cone by a parabolic reflector.

11. Apparatus for detecting floating pollutants from the class consisting of diesel/fuel oil, lube oil, motor oil, hydraulic oil, jet fuel, mineral oil and crude oil floating on a water surface, which apparatus comprises:
a structure for mounting vertically above the surface of a body of water,
a pulsed light source supported by said mounting structure,
means supported by said mounting structure for directing said pulses of light from said source vertically downward toward a target said water surface, and for filtering said pulses to produce a beam of light, limited to wavelengths between about 225 and 300 nm, which beam is an outwardly spreading cone of light rays having an apex angle between about 13 and 15° where the centerline of said cone is aligned within about 7° of vertical,
a photodetector supported by said structure for detecting fluorescent light that would be emitted from said pollutants floating on said water surface,
filter means supported by said structure that allows direct line of sight passage from said floating pollutants on said water surface to said photodetector of only light having a wavelength between about 320 to 400 nm,
means for analyzing data detected by said photodetector to determine the presence of even small quantities of floating pollutants within said class, and
means for promptly reporting and/or producing a signal or alarm when said analyzed data indicates the presence of any significant amount of one said pollutant.

* * * * *